United States Patent
Coter

(10) Patent No.: US 7,688,677 B2
(45) Date of Patent: Mar. 30, 2010

(54) SYSTEM AND METHOD FOR DETERMINING PROPERTIES OF TUBULAR CAVITY

(75) Inventor: Florin Coter, Haifa (IL)

(73) Assignee: BioScan Ltd, Yokneam (IL)

( * ) Notice: Subject to any disclaimer, the term of this patent is extended or adjusted under 35 U.S.C. 154(b) by 570 days.

(21) Appl. No.: 10/521,595

(22) PCT Filed: Jul. 15, 2003

(86) PCT No.: PCT/IL03/00584

§ 371 (c)(1),
(2), (4) Date: Oct. 6, 2005

(87) PCT Pub. No.: WO2004/008070

PCT Pub. Date: Jan. 22, 2004

(65) Prior Publication Data

US 2008/0210011 A1    Sep. 4, 2008

(30) Foreign Application Priority Data

Jul. 16, 2002    (IL) .................................. 150748

(51) Int. Cl.
G01S 15/00    (2006.01)
G01N 29/024    (2006.01)
A61B 8/14    (2006.01)

(52) U.S. Cl. .................... 367/99; 73/623; 73/597; 600/462

(58) Field of Classification Search ............. 367/99; 73/597, 614, 622, 623; 600/462, 463
See application file for complete search history.

(56) References Cited

U.S. PATENT DOCUMENTS

| 3,542,014 | A | 11/1970 | Peronneau |
| 4,947,852 | A | 8/1990 | Nassi et al. |
| 6,585,656 | B2 * | 7/2003 | Masters ............. 600/466 |
| 6,685,644 | B2 | 2/2004 | Seo et al. |
| 7,037,271 | B2 * | 5/2006 | Crowley ............. 600/463 |

OTHER PUBLICATIONS

International Search Report WO 2004/008070 A3, Jan. 22, 2004.

* cited by examiner

*Primary Examiner*—Ian J Lobo
(74) *Attorney, Agent, or Firm*—Pearl Cohen Zedek Latzer, LLP

(57) ABSTRACT

A method for determining the distance of a transceiver located within a lumen from the center of the lumen and for determining the radius of the lumen, the lumen cross-section being substantially circular at the transceiver location, the method applied on data received from a transceiver placed at a position within the lumen that is distance (r) from the center and distance (a) from the lumen wall, transmitting a signal of known velocity (v) that can be correlated with the time of flight and receiving a first signal and a second signal that are reflections of the transmitted signal, timing the time differences between the transmission of the transmitted signal and reception of the first (t1) and second (t2) reflection signals, the method comprising: Calculating the distance of the transceiver from the center of the lumen=(t1−t2)v/4; and Calculating the radius of the lumen=(t1+t2)v/4.

1 Claim, 1 Drawing Sheet

SYSTEM AND METHOD FOR DETERMINING PROPERTIES OF TUBULAR CAVITY

CROSS-REFERENCE TO RELATED APPLICATIONS

This application is a National Phase Application of PCT International Application No. PCT/IL2003/000584, International Filing Date Jul. 15, 2003, claiming priority of Israeli Patent Application, 150748, filed Jul. 16, 2002, which are both incorporated by reference herein in their entirety.

FIELD OF THE INVENTION

The present invention relates to determining properties of a tubular cavity including the location of a device inserted into the cavity.

BACKGROUND OF THE INVENTION

In many fields there is a need to determine information about the cavity of tubular structures, such as blood vessels or pipelines. This information can include the thickness of the walls, the maximum and minimum internal diameters, and the location of a device inserted into the cavity relative to the cavity.

In anatomy the cavities of such tubular organs (for example veins and arteries) are called lumens. A typical prior art solution for analyzing lumen geometry and navigating within them has been to use ultrasound. For example, in an ultrasound coronary investigation a full circle scan (2D) is used in order to estimate the lumen size of a blood vessel. To achieve the estimate requires a large amount of computational power and involves sophisticated image processing schemes.

The present invention proposes a simple method for determining lumen properties by analyzing signals from a device placed inside the lumen.

In summary, it is a main object of the present invention to provide a method for analyzing signals from a device inside a tubular cavity to determine properties of the cavity including the location of the device.

The calculating power required for the present invention is significantly less that that required for conventional image processing methods, generally two orders of magnitude less.

Still further objects and advantages will become apparent from a consideration of the ensuing description and drawings.

BRIEF DESCRIPTION OF THE INVENTION

There is thus provided, in accordance with a preferred embodiment of the present invention, A computer based method for determining the distance of a transceiver located within a lumen from the center of the lumen and for determining the radius of the lumen, the lumen cross-section being substantially circular at the transceiver location, the method applied on data received from a transceiver placed at a position within the lumen that is distance (r) from the center and distance (a) from the lumen wall, transmitting a signal of known velocity (v) that can be correlated with the time of flight and receiving a first signal and a second signal that are reflections of the transmitted signal, timing the time differences between the transmission of the transmitted signal and reception of the first (t1) and second (t2) reflection signals, the method comprising:

a. Calculating the distance of the transceiver from the center of the lumen=$(t1-t2)v/4$;
b. Calculating the diameter of the lumen=$(t1+t2)v/2$;

BRIEF DESCRIPTION OF THE FIGURES

The invention is described herein, by way of example only, with reference to the accompanying Figures, in which like components are designated by like reference numerals.

DETAILED DESCRIPTION OF THE INVENTION

The present invention proposes a simple method for determining lumen properties by analyzing signals from a device placed inside the lumen. The device is assumed to be a transducer and the signals are assumed to be ultrasound. However the signals can be any signal that can be correlated with its time of flight.

Ultrasound measurements consist of an emission of a sound at very high frequency, listening to the echo, and analyzing the echo structure. Blood vessel wall reflects ultrasound, thus enabling good distance measurement. Various components of the blood system reflect ultrasound waves as well, but with different efficiencies, i.e. intensities, noise, etc. The sum of those differences provide information about the blood vessel and the lumen.

Ultrasound measurements comprise a simple procedure:
Emission of a short pulse of acoustic energy
Exact registration of the emission time
"Listening" to echoes (multiple reflections)
Electronic and mathematical signal manipulations
Echo classification
Distance (arrival time) estimates
Display in terms of image and/or numbers.

Ultrasound is basically a pressure wave or wave packet and behaves according to simple laws of optics. We do not refer here to nonlinear effects like cavitations, frequency dispersion, etc.

Consequently, we can define our physical system as comprising a pulse source (ultrasound emitter), a non-dispersive propagation medium, a cylindrical reflector and a receiver (ultrasound receiver). The reflector has two types of influence on the impinging waves:

Reflection: like any other surface it reflects according to the geometry and impinging angles.

Spatial dispersion: some energy will be reflected around the reflection angle, thus a Lambertian element will be present in the reflection pattern. (A Lambertian reflector is characterized by reflection intensity different from zero at angles other than reflection angle. The reflection pattern resembles a lobe shape oriented along the reflection direction. The more is the reflector Lambertian in nature, the more wide the pear shape will be. A perfect Lambertiam reflector reflects light with equal intensity at all angles disregarding the direction of the impinging light.)

The system has a cylindrical symmetry, hence a plane model will suffice.

The mathematical equations are developed according to the following assumptions:

Ultrasound source is a point and has a constant angular radiation pattern.

Ultrasound receiver is a point and has a constant angular sensitivity pattern.

Reflector is a circle with a perfectly reflecting mirror-like surface.

There is no intensity attenuation

Figure 1:
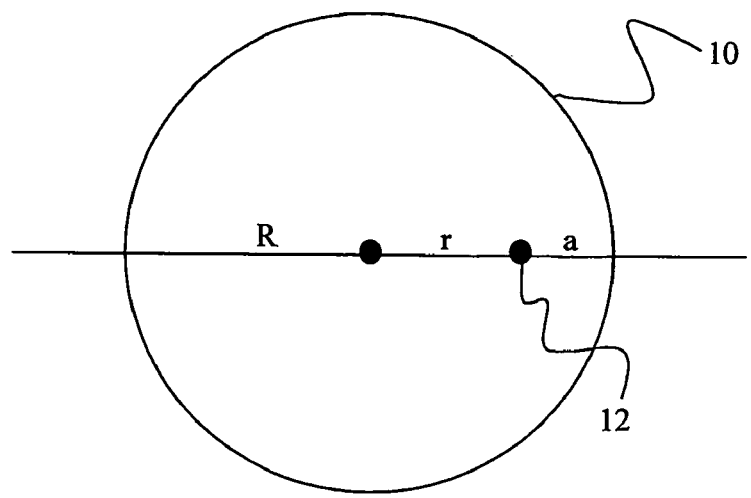
FIG. 1 illustrates a model of the geometry of a lumen with a transceiver inside it.

The mathematical model is indeed very simple as only two algebraic equations are used. The geometry of the model is shown in FIG. 1. Lumen (circle) 10 has a radius (R). Transceiver 12 (comprising a transmitter and a receiver, both having no effective spatial extension) is located at a distance (a) from the lumen perimeter and at a distance (r) from the center.

Within the framework of the model, waves are reflected from a specular surface according to the laws of geometric optics. The reflecting surface has a circular shape. Waves emerging from the transmitter will bounce from the surface at equal angles with respect to the normal at the surface at the same point. Since normal lines at circle are passing through the center they are the same as diameters. Hence only reflections along the diameter passing through the transducer will reach the receiver. Hence, a receiver can detect only waves coming from the peripheral points located along the line connecting the circle center and the detector. This line intersects the circle at two points. Only waves from these points will be detected by the receiver.

One wave is reflected by the near side and is received at a time given by $$t_1 = \frac{2 \cdot (R-r)}{v} \quad (1)$$

where v is the sound velocity in the medium.

The second wave is reflected by the far side and is received at a time is given by $$t_2 = \frac{2 \cdot (r+R)}{v} \quad (2)$$

Solving the two equations one has the distance between the transducer (emitter and receiver) α and the reflector radius R as:

$$r = \frac{(t_1 - t_2) \cdot v}{4} \quad (3)$$

$$R = \frac{(t_1 + t_2) \cdot v}{4} \quad (4)$$

The two numbers given by equations (3) and (4) provide all the needed information:

r—the location of the transducer within the circle.

R—The circle radius

Thus, from a very simple measurement one can provide the "navigation" map in terms of path size and location on the path.

Figure 2:
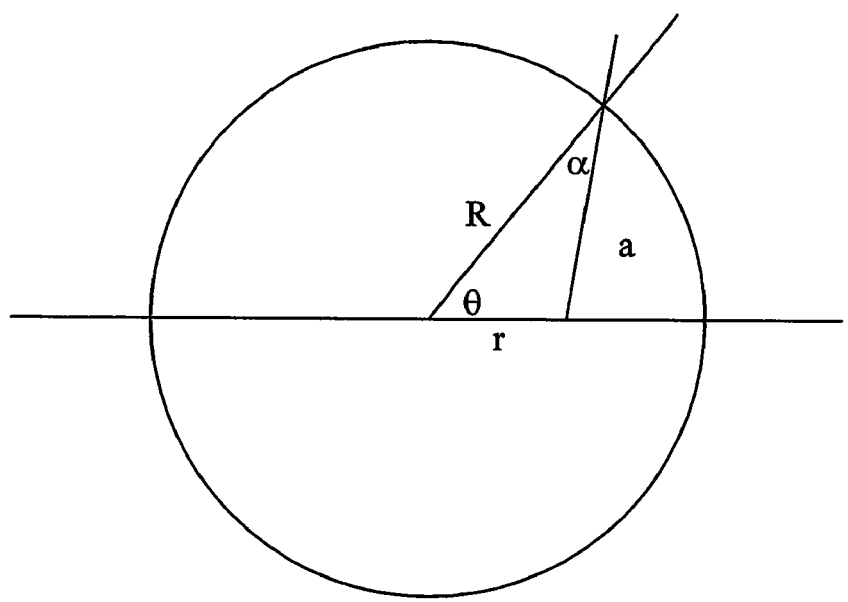
FIG. 2 illustrates a model of the geometry of a lumen with a transceiver inside it taking into account angular reflections along the reflection direction

An assumption that can be discarded is the specular mirror nature of the reflector. A more realistic assumption is a surface that has some angular reflections along the reflection direction, i.e. it is Lambertian to some extension. This can be taken into account using the model in FIG. 2. The equations (1) and (2) must be modified to:

$$r \cdot \cos\theta + \alpha \cdot \cos\alpha = R \quad (5)$$

$$r \cdot \sin\theta = \alpha \cdot \sin\alpha \quad (6)$$

After some simple calculations one finds:

$$\alpha = \sqrt{R^2 + r^2 - 2 \cdot r \cdot R \cdot \cos\theta} \quad (7)$$

Equation (7) reflects the simple fact that for a variation of the angle θ between 0 and 180°, α is monotonously increasing. The significance is crucial: The arrival time of every reflection is correlated to the reflection geometry. From the point of view of the mirror model this means that all the reflections from other points not on the center-to-transducer line will reach the transducer at times between $t_1$ and $t_2$ in an ordered manner.

One should mention that a secondary reflection traveling twice the diameter can be detected. Time of flight is precisely four times the result in eq. (4). The numerical result is independent of the transducer position inside the lumen.

If one assumes a narrow Lambertian distribution around the reflection angles, then only the small angles reflections will significantly contribute to the line widths.

Another factor to be taken into account is the optical distortion caused by large field of view in the case where the receiver and transmitter are not the same mathematical point). This effect will contribute to some line widening.

Calculated ultrasound signal shows clearly that the main contribution is connected to the line width.

It should be clear that the description of the embodiments and attached Figures set forth in this specification serves only for a better understanding of the invention, without limiting its scope.

It should also be clear that a person skilled in the art, after reading the present specification could make adjustments or amendments to the attached Figures and above described embodiments that would still be covered by the scope of the present invention.

The invention claimed is:

1. A method for determining the distance of a transceiver located within a lumen from the center of the lumen and for determining the radius of the lumen, the lumen cross-section being substantially circular at the transceiver location, the method applied on data received from a transceiver placed at a position within the lumen that is distance (r) from the center, the method comprising:

transmitting a signal of known velocity (v);

receiving two echo signals, the first signal related to a near section of the lumen and the second signal related to an outermost section of the lumen;

timing a first time difference between the transmission time of the transmitted signal and reception time of the first echo signal (t1) and a second time difference between the transmission time of the transmitted signal and the reception time of the second echo signal (t2);

calculating the distance of the transceiver from the center of the lumen r using the equation r=(t1−t2)v/4; and calculating the radius of the lumen R using the equation R=(t1+t2)v/4.

* * * * *